(12) United States Patent  
Miyao et al.

(10) Patent No.: US 9,274,069 B2  
(45) Date of Patent: *Mar. 1, 2016

(54) METHOD FOR EVALUATING DEGREE OF CRYSTALLINE ORIENTATION OF POLYCRYSTALLINE SILICON, METHOD FOR SELECTING POLYCRYSTALLINE SILICON ROD, POLYCRYSTALLINE SILICON ROD, POLYCRYSTALLINE SILICON INGOT, AND METHOD FOR MANUFACTURING MONOCRYSTALLINE SILICON

(71) Applicant: Shin-Etsu Chemical Co., Ltd., Tokyo (JP)

(72) Inventors: Shuichi Miyao, Niigata (JP); Junichi Okada, Niigata (JP); Shigeyoshi Netsu, Niigata (JP)

(73) Assignee: SHIN-ETSU CHEMICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/409,202

(22) PCT Filed: Jun. 18, 2013

(86) PCT No.: PCT/JP2013/003791  
§ 371 (c)(1),  
(2) Date: Dec. 18, 2014

(87) PCT Pub. No.: WO2013/190829  
PCT Pub. Date: Dec. 27, 2013

(65) Prior Publication Data  
US 2015/0185167 A1 Jul. 2, 2015

(30) Foreign Application Priority Data  
Jun. 18, 2012 (JP) .................................. 2012-136849

(51) Int. Cl.  
*C30B 29/06* (2006.01)  
*G01N 23/20* (2006.01)  
(Continued)

(52) U.S. Cl.  
CPC ................ *G01N 23/20* (2013.01); *C01B 33/02* (2013.01); *C01B 33/021* (2013.01);  
(Continued)

(58) Field of Classification Search  
CPC .......... C30B 28/00; C30B 29/06; C30B 33/00  
See application file for complete search history.

(56) References Cited

U.S. PATENT DOCUMENTS 5,414,747 A 5/1995 Ruud et al.  
5,976,481 A 11/1999 Kubota et al.  
(Continued)

FOREIGN PATENT DOCUMENTS

CN 1088444 C 7/2002  
CN 101815671 A 8/2010  
(Continued)

OTHER PUBLICATIONS

International Search Report issued Aug. 13, 2013 in PCT/JP2013/003791 Filed Jun. 18, 2013.

(Continued)

*Primary Examiner* — Robert M Kunemund  
(74) *Attorney, Agent, or Firm* — Oblon, McClelland, Maier & Neustadt, L.L.P.

(57) ABSTRACT

When the degree of crystalline orientation of polycrystalline silicon is evaluated by an X-ray diffraction method, each obtained disc-like sample 20 is disposed in a position where Bragg reflection from a Miller index face <hkl> is detected and in-plane rotated at a rotational angle φ with the center of the disc-like sample 20 as the center of rotation, so that an X-ray-radiated region defined by a slit φ-scans over the principal surface of the disc-like sample 20, to determine a chart representing the dependence of the intensity of Bragg reflection from the Miller index face <hkl> on the rotational angle (φ) of the disc-like sample 20, a baseline is determined from the chart, and the diffraction intensity value of the baseline is used as an estimative index of the degree of crystalline orientation.

20 Claims, 6 Drawing Sheets

(51) Int. Cl.
  *C01B 33/035* (2006.01)
  *C01B 33/021* (2006.01)
  *C30B 13/00* (2006.01)
  *C01B 33/02* (2006.01)
  *C30B 29/60* (2006.01)
  *G01N 23/207* (2006.01)

(52) U.S. Cl.
  CPC .............. *C01B 33/035* (2013.01); *C30B 13/00* (2013.01); *C30B 29/06* (2013.01); *C30B 29/605* (2013.01); *G01N 23/207* (2013.01); *G01N 2223/3306* (2013.01); *G01N 2223/606* (2013.01)

(56) References Cited

U.S. PATENT DOCUMENTS

| | | | |
|---|---|---|---|
| 8,049,100 B2 * | 11/2011 | Clark et al. | 136/257 |
| 2005/0190880 A1 | 9/2005 | Yokoyama et al. | |
| 2008/0286550 A1 | 11/2008 | Sofin et al. | |
| 2009/0324819 A1 | 12/2009 | Kulkarni et al. | |
| 2010/0219380 A1 | 9/2010 | Hertlein et al. | |
| 2012/0175613 A1 | 7/2012 | Netsu et al. | |
| 2012/0201976 A1 | 8/2012 | Netsu et al. | |
| 2013/0102092 A1 | 4/2013 | Netsu et al. | |
| 2014/0033966 A1 | 2/2014 | Miyao et al. | |

FOREIGN PATENT DOCUMENTS

| | | |
|---|---|---|
| CN | 102076607 A | 5/2011 |
| CN | 102498064 A | 6/2012 |
| EP | 2 692 909 A1 | 2/2014 |
| JP | 37-18861 B | 12/1962 |
| JP | 2-266249 A | 10/1990 |
| JP | 3-20651 A | 1/1991 |
| JP | 4-022218 B2 | 4/1992 |
| JP | 2006-071377 A | 3/2006 |
| JP | 2006-89353 A | 4/2006 |
| JP | 2008-285403 A | 11/2008 |
| JP | 2012-17997 A | 1/2012 |
| WO | WO 2012/164803 A1 | 12/2012 |
| WO | 2013/150758 A1 | 10/2013 |

OTHER PUBLICATIONS

Supplementary European Search report dated Oct. 14, 2015 issued in EP 13806297.1.
Office Action dated Oct. 28, 2015 issued in corresponding Chinese patent application No. 201380032180.5.

* cited by examiner

METHOD FOR EVALUATING DEGREE OF CRYSTALLINE ORIENTATION OF POLYCRYSTALLINE SILICON, METHOD FOR SELECTING POLYCRYSTALLINE SILICON ROD, POLYCRYSTALLINE SILICON ROD, POLYCRYSTALLINE SILICON INGOT, AND METHOD FOR MANUFACTURING MONOCRYSTALLINE SILICON

TECHNICAL FIELD

The present invention relates to a method for evaluating the degree of crystalline orientation of polycrystalline silicon, and a method for selecting a suitable non-orientational polycrystalline silicon rod or ingot as a raw material for stably manufacturing monocrystalline silicon utilizing the evaluating method.

BACKGROUND ART

Monocrystalline silicon essential for the manufacture of semiconductor devices and the like is grown by a CZ method or an FZ method, and a polycrystalline silicon rod or a polycrystalline silicon ingot is used as a raw material at that time. Such polycrystalline silicon materials are manufactured by a Siemens method in most cases (see, for example, Patent Literature 1). The Siemens method is a method for bringing a silane raw material gas, such as trichlorosilane or monosilane, into contact with a heated silicon core wire to vapor phase-grow (deposit) polycrystalline silicon on the surfaces of the silicon core wire by a CVD (Chemical Vapor Deposition) method.

For example, a polycrystalline silicon ingot is charged into a quartz crucible when monocrystalline silicon is grown by a CZ method, and a seed crystal is immersed in a silicon melt into which this ingot has been heat-melted to annihilate dislocation lines (make the seed silicon dislocation-free). Thereafter, the seed silicon is gradually increased in diameter until a predetermined diameter is reached, and crystal pull-up is performed. If any unmelted polycrystalline silicon remains in the silicon melt at this time, pieces of this unmelted polycrystalline silicon drift in the vicinity of a solid-liquid interface due to convection. Thus, these polycrystalline pieces may be a cause for the induction of dislocation generation and the loss of crystal lines.

In addition, in Patent Literature 2, there is pointed out a problem in which acicular crystal may deposit within a polycrystalline silicon rod (polycrystalline silicon bar) in a process for manufacturing the rod by a Siemens method and, if monocrystalline silicon is grown by an FZ method using such a polycrystalline silicon rod, individual crystallites do not melt uniformly according to their sizes due to the abovementioned non-uniform microstructure, and unmelted crystallites pass through a melt zone as solid particles into a monocrystalline rod as unmelted particles to be incorporated into coagulated surfaces of a monocrystal, thus causing defect formation.

For this problem, Patent Literature 2 proposes a technique of grinding or polishing surfaces of a sample cut out perpendicularly to the long-axis direction of the polycrystalline silicon rod, measuring the size and area ratio of acicular crystal by enhancing the contrast to the extent of being able to visually recognize the microcrystallites of a composition even under an optical microscope after etching, and determining the acceptance/rejection of the rod as a raw material for producing FZ monocrystalline silicon on the basis of the results of measurement.

CITATION LIST

Patent Literatures

Patent Literature 1: Japanese Patent Publication No. 37-18861

Patent Literature 2: Japanese Patent Laid-Open No. 2008-285403

SUMMARY OF INVENTION

Technical Problem

However, such visual determination of acceptance/rejection under an optical microscope as described in the technique disclosed in Patent Literature 2 is not only liable to cause differences in determination results, depending on, for example, the degree of etching of the observed surfaces of a sample and the observation skills of a person in charge of evaluation, but also inferior in quantitativeness and repeatability. Accordingly, acceptance/rejection criteria need to be set to a somewhat higher level from the viewpoint of increasing the manufacturing yield of monocrystalline silicon. As a result, the rejection rate of polycrystalline silicon rods becomes higher.

In addition, a study made by the present inventors has revealed that even when a polycrystalline silicon rod determined to be an accepted unit is used, dislocation can occur in a process for growing the monocrystalline silicon rod by an FZ method and crystal lines may be lost in the technique disclosed in Patent Literature 2.

Consequently, a technique to select polycrystalline silicon suitable as a raw material for the manufacture of monocrystalline silicon with high degrees of quantitativeness and repeatability is required, in order to stably manufacture monocrystalline silicon at a high yield rate.

The present invention has been accomplished in view of such problems as described above. Accordingly, an object of the present invention is to provide a technique of selecting polycrystalline silicon suitable as a raw material for the manufacture of monocrystalline silicon with high degrees of quantitativeness and repeatability and contributing to the stable manufacture of monocrystalline silicon.

Solution to Problem

In order to achieve the above-described object, a method for evaluating the degree of crystalline orientation of polycrystalline silicon according to the present invention is a method for evaluating the degree of crystalline orientation of polycrystalline silicon by an X-ray diffraction method, the evaluating method including: forming the polycrystalline silicon into a plate-like sample; disposing the plate-like sample in a position where Bragg reflection from a Miller index face <hkl> is detected; performing in-plane rotation of the plate-like sample at a rotational angle $\phi$ with the center of the plate-like sample as the center of rotation, so that an X-ray-radiated region defined by a slit $\phi$-scans over the principal surface of the plate-like sample, to determine a chart representing the dependence of the intensity of Bragg reflection from the Miller index face <hkl> on the rotational angle ($\phi$) of the plate-like sample; determining a baseline from the chart; and using the diffraction intensity value of the baseline as the estimative index of the degree of crystalline orientation.

Preferably, the Miller index face <hkl> is at least one of <111> and <220>.

A method for selecting a polycrystalline silicon rod according to the present invention is a method for selecting a polycrystalline silicon rod to be used as a raw material for the manufacture of monocrystalline silicon using an X-ray diffraction method, in which the polycrystalline silicon rod is grown by means of deposition based on a chemical vapor deposition method, the selecting method including: obtaining two or more plate-like samples having a cross-section perpendicular to the radial direction of the polycrystalline silicon rod as a principal surface; disposing the plate-like samples in a position where Bragg reflection from a Miller index face <hkl> is detected; performing in-plane rotation of the plate-like samples at a rotational angle φ with the center of the plate-like sample as the center of rotation, so that an X-ray-radiated region defined by a slit φ-scans over the principal surface of the plate-like sample, to determine a chart representing the dependence of the intensity of Bragg reflection from the Miller index face <hkl> on the rotational angle (φ) of the plate-like sample; determining baselines from the chart; and determining suitability/unsuitability as a raw material for the manufacture of monocrystalline silicon is determined using the results of comparison between or among diffraction intensity values of the baselines obtained from the respective two or more plate-like samples as criteria.

Preferably, the Miller index face <hkl> is at least one of <111> and <220>.

The above-described method for selecting a polycrystalline silicon rod may be embodied such that the Miller index face <hkl> is <111>, and the method further includes determining the diffraction intensity value of the baseline of the chart obtained by performing the φ-scan for each of the two or more plate-like samples and selecting the polycrystalline silicon rod as a raw material for the manufacture of monocrystalline silicon if a value given by dividing the maximum value of the plurality of baseline diffraction intensity values by the minimum value thereof is 1.5 or smaller.

The method may also be embodied such that the Miller index face <hkl> is <220>, and the method further includes determining the diffraction intensity value of the baseline of the chart obtained by performing the φ-scan for each of the two or more plate-like samples and selecting the polycrystalline silicon rod as a raw material for the manufacture of monocrystalline silicon if a value given by dividing the maximum value of the plurality of baseline diffraction intensity values by the minimum value thereof is 1.9 or smaller.

The method may further includes: performing the φ-scan on both the Miller index faces <111> and <220> for each of the two or more plate-like samples; dividing the diffraction intensity value ($I^{<111>}$) of the baseline of a chart obtained with respect to the Miller index face <111> by the diffraction intensity value ($I^{<220>}$) of the baseline of a chart obtained with respect to the Miller index face <220> to determine a value (division value: $I^{<111>}/I^{<220>}$); and selecting the polycrystalline silicon rod as a raw material for the manufacture of monocrystalline silicon if the maximum value of a plurality of the division values determined from the two or more plate-like samples is smaller than 2.5.

Examples of cases where the method according to the present invention is particularly useful include a case in which the polycrystalline silicon rod is grown by a Siemens method.

In the present invention, a polycrystalline silicon rod selected by the above-described method and this rod is used as a silicon feedstock to manufacture monocrystalline silicon, or a polycrystalline silicon ingot obtained by crushing the selected polycrystalline silicon rod is used as a silicon feedstock to manufacture monocrystalline silicon. Consequently, it is possible to prevent the occurrence of a problem in which crystal lines are lost in single-crystallization.

Advantageous Effect of Invention

A polycrystalline silicon rod selected by the method of the present invention is a "non-oriented" rod low in the degree of crystalline orientation. Accordingly, the local generation of partial unmelted residues is prevented if crystal growth is carried out by an FZ method using such a polycrystalline silicon rod or if crystal growth is carried out by a CZ method using a polycrystalline silicon ingot obtained by crushing the polycrystalline silicon rod. Thus, it is possible to stably manufacture monocrystalline silicon.

DESCRIPTION OF EMBODIMENTS

In the course of study on the quality improvement of polycrystalline silicon for the purpose of stably manufacturing monocrystalline silicon, the present inventors have gained the knowledge that the degree of crystalline orientation within a polycrystalline silicon rod differs depending on the conditions under which polycrystalline silicon deposits. Unlike monocrystalline silicon, a block of polycrystalline silicon contains a large number of crystal grains, and these crystal grains tend to be considered as being oriented at random.

According to a study made by the present inventors, however, the crystal grains contained in the polycrystalline silicon block are not always completely randomly-oriented.

In a powder sample obtained by crushing a polycrystalline silicon block, individual silicon crystal grains can be treated as being completely randomly-oriented. In fact, Bragg reflection intensity remains substantially constant even if the powder sample is disposed in a position where Bragg reflection from a specific Miller index face <hkl> is detected and in-plane rotated with the center of the sample as the center of rotation, so that an X-ray-radiated region defined by a slit scans over the entire surface of the powder sample, and an observed value is almost linear on a chart when a 2θ measurement is performed.

On the other hand, the present inventors have taken plate-like samples having a cross-section perpendicular to the radial direction of each polycrystalline silicon rod as a principal surface from many different polycrystalline silicon rods grown by means of deposition using a chemical vapor deposition method, and examined the intensity of Bragg reflection from a Miller index face <hkl> in the same way as described above. Then, the examination has revealed the fact that a chart of the intensity of Bragg reflection from the Miller index face <hkl> shows large and small peaks and the value (intensity) of the baseline of the chart varies from one sample to another, depending on the conditions of manufacturing the polycrystalline silicon rods.

In addition, a study made by the present inventors has proved that when an attempt is made on single-crystallization by an FZ method using each polycrystalline silicon rod as a raw material by taking samples from many polycrystalline silicon rods (silicon bars) and performing the above-described measurement of Bragg reflection intensity, crystal lines are not lost in a single-crystallization process if the diffraction intensity value of the baseline appearing on the abovementioned chart of Bragg reflection intensity satisfies a specific condition, whereas the crystal lines are highly likely to be lost in the single-crystallization process if the diffraction intensity value does not satisfy this specific condition. Note that the condition that the diffraction intensity value of the abovementioned baseline satisfies will be described later.

That is, the degree of crystalline orientation (non-random orientation) depends on conditions under which polycrystalline silicon deposits, and crystal grains within a polycrystalline silicon rod are not always randomly-oriented. In addition, it has turned out that if a polycrystalline silicon rod or a polycrystalline silicon ingot low in the degree of randomness of crystalline orientation (high in the degree of crystalline orientation) is used as a raw material for the manufacture of monocrystalline silicon, partial unmelted residues may be generated locally, thus inducing dislocation generation and possibly causing the loss of crystal lines.

When polycrystalline silicon rods are manufactured, the amount of raw material supplied per surface area and the state of surface temperature vary along with the growth of each silicon rod. Consequently, the regional dependence of the orientation of crystal grains in the long-axis direction of the silicon rod tends to be higher than the regional dependence of the orientation of crystal grains in the radial direction of the silicon rod.

Hence, a cylindrical sample having a central axis in the radial direction of one polycrystalline silicon rod is obtained from the rod. A plurality of plate-like samples (disc-like samples) having a cross-section perpendicular to the radial direction of the polycrystalline silicon rod as a principal surface is sliced and taken from different locations of this cylindrical sample. Then, a 2θ measurement of Bragg reflection intensity is performed for each plate-like sample. Thus, it is possible to estimate the state of the orientation of crystal grains of the silicon rod as a whole by comparing the charts of Bragg reflection intensity of those samples.

In addition, it is estimated that if the regional dependence of crystalline orientation within the silicon rod is lower than a certain degree, melting and solidification progress in a uniform manner in a single-crystallization process using such a polycrystalline silicon rod as a raw material and, consequently, loss of crystal lines does not occur.

Hereinafter, embodiments of the present invention will be described while referring to the accompanying drawings.

Figure 1A:
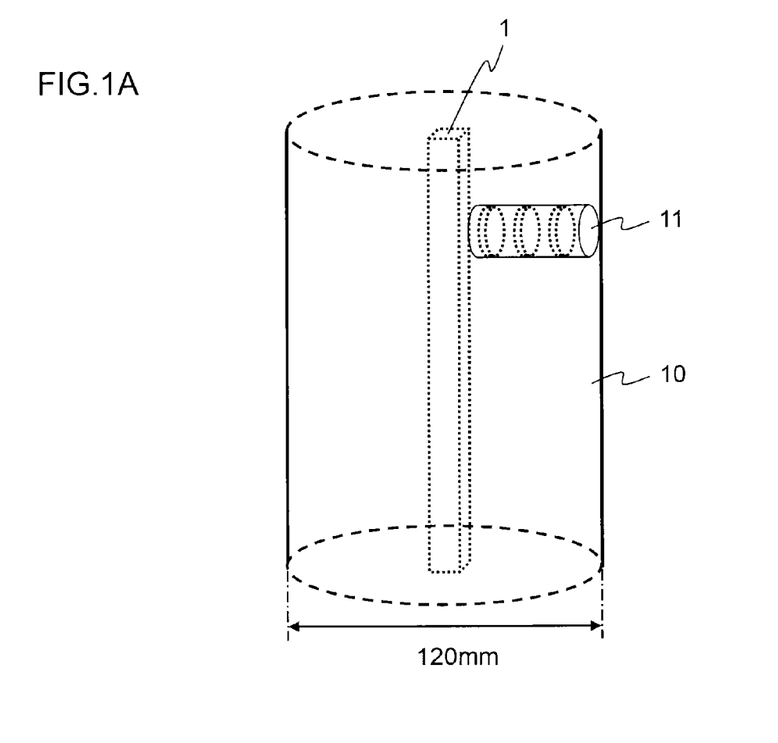
FIG. 1A is a drawing used to describe an example of taking plate-like samples for X-ray diffraction measurement from a polycrystalline silicon rod deposited and grown by a chemical vapor deposition method.
Figure 1B:
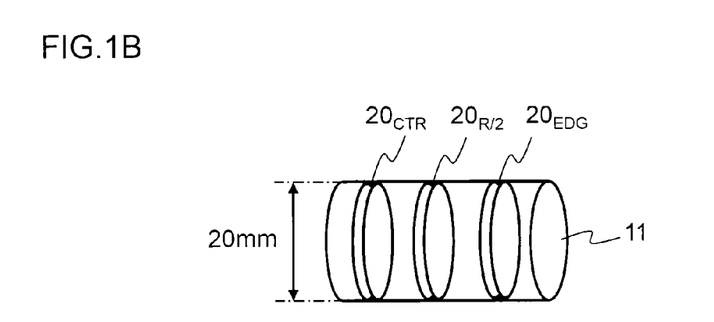
FIG. 1B is a drawing used to describe an example of taking plate-like samples for X-ray diffraction measurement from a polycrystalline silicon rod deposited and grown by a chemical vapor deposition method.

FIGS. 1A and 1B are drawings used to describe an example of taking plate-like samples 20 for the measurement of X-ray diffraction profiles from a polycrystalline silicon rod 10 deposited and grown by a chemical vapor deposition method, such as a Siemens method. In the figures, reference numeral 1 denotes a silicon core wire used to deposit polycrystalline silicon on the surfaces of the core wire to form a silicon rod. Note that in this example, the plate-like samples 20 are taken from three locations (CTR: a location close to the silicon core wire 1, EDG: a location close to the side surface of the polycrystalline silicon rod 10, and R/2: a location intermediate between the CTR and the EGD), in order to verify whether or not the degree of crystalline orientation of the polycrystalline silicon rod has radial-direction dependence. The present embodiment is, however, not limited to sampling from these locations.

The diameter of the polycrystalline silicon rod 10 illustrated in FIG. 1A is approximately 120 mm. From the lateral side of this polycrystalline silicon rod 10, a rod 11, approximately 20 mm in diameter and approximately 60 mm in length, is cut and pulled out perpendicularly to the longitudinal direction of the silicon core wire 1.

Then, as illustrated in FIG. 1B, approximately 2 mm-thick disc-like samples ($20_{CTR}$, $20_{EDG}$, and $20_{R/2}$) having a cross-section perpendicular to the radial direction of the polycrystalline silicon rod 10 as a principal surface are taken from the location (CTR) close to the silicon core wire 1 of this rod 11, the location (EDG) close to the lateral side of the polycrystalline silicon rod 10, and the location (R/2) intermediate between the CTR and the EGD, respectively.

Note that a location from which the rod 11 is sampled, the length of the rod 11, and the number of the rods 11 may be determined as appropriate, according to the diameter of the silicon rod 10 and the diameter of the rod 11 to be cut and pulled out. Although the disc-like sample 20 may also be taken from any locations of the cut and pulled-out rod 11, it is preferable that the locations are where the characteristics of the silicon rod 10 as a whole can be reasonably estimated. For example, when two disc-like samples are taken, the samples are preferably taken from two locations, i.e., locations positioned closer to and farther from the center side of the silicon rod than a point half the radius thereof from the center with respect to the circumferential radius of the silicon rod. In addition, if, for example, the locations from where two samples to be compared are taken are specified as a location positioned closer to the center side than a point one-third the radius from the center and a location positioned farther from the center side than a point two-thirds the radius from the center, it is possible to make a more precise comparison. Yet additionally, the number of disc-like samples to be compared may be any number equal to or larger than two, and there is no upper limit in particular.

Although the diameter of the disc-like samples 20 is specified as approximately 20 mm, the diameter is merely an example. Accordingly, the diameter may be determined as appropriate, so as not to cause any problems at the time of X-ray diffraction measurement.

In the present invention, when the degree of crystalline orientation of polycrystalline silicon is evaluated by an X-ray diffraction method, each disc-like sample 20 taken as described above is disposed in a position where Bragg reflection from a Miller index face <hkl> is detected and in-plane rotated at a rotational angle φ with the center of the disc-like sample 20 as the center of rotation, so that an X-ray-radiated region defined by a slit φ-scans over the principal surface of the disc-like sample 20, to determine a chart representing the dependence of the intensity of Bragg reflection from the Miller index face <hkl> on the rotational angle (φ) of the disc-like sample 20, a baseline is determined from the chart, and the diffraction intensity value of the baseline is used as an estimative index of the degree of crystalline orientation.

In addition, in the present invention, a polycrystalline silicon rod suitable as a raw material for the manufacture of monocrystalline silicon is selected using the above-described method for evaluating the degree of crystalline orientation of polycrystalline silicon.

That is, a method for selecting a polycrystalline silicon rod according to the present invention is a method for selecting a polycrystalline silicon rod used as a raw material for the manufacture of monocrystalline silicon using an X-ray diffraction method, in which the polycrystalline silicon rod is grown by means of deposition based on a chemical vapor deposition method, and the method includes obtaining two or more plate-like samples having a cross-section perpendicular to the radial direction of the polycrystalline silicon rod as a principal surface; disposing the plate-like samples in a position where Bragg reflection from a Miller index face <hkl> is detected; performing in-plane rotation of the plate-like samples at a rotational angle φ with the center of the plate-like sample as the center of rotation, so that an X-ray-radiated region defined by a slit φ-scans over the principal surface of the plate-like sample, to determine charts representing the dependence of the intensity of Bragg reflection from the Miller index face <hkl> on the rotational angle (φ) of the plate-like sample; determining a baseline from the chart; and determining suitability/unsuitability as a raw material for the manufacture of monocrystalline silicon using the results of comparison between or among diffraction intensity values of the baselines obtained from the respective two or more plate-like samples as criteria.

Preferably, the Miller index face <hkl> is at least one of <111> and <220>.

Figure 2:
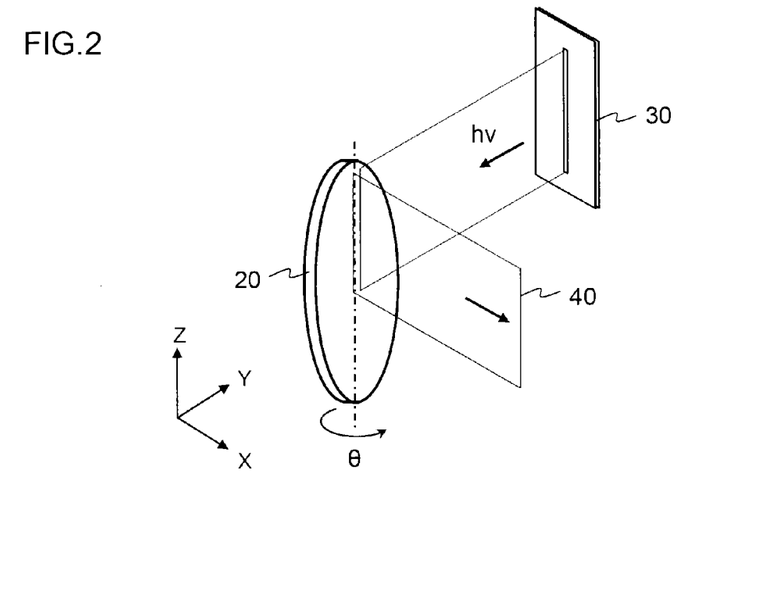
FIG. 2 is a drawing used to describe an outline of a measurement system used when a profile of X-ray diffraction from a plate-like sample is determined by a θ-2θ method.

FIG. 2 is a drawing used to describe an outline of a measurement system used when a profile of X-ray diffraction from a disc-like sample 20 is determined by a so-called θ-2θ method. An X-ray beam 40 (Cu-Kα ray with a wavelength of 1.54 angstroms) emitted from a slit 30 and collimated enters the disc-like sample 20. The intensity of the diffracted X-ray beam is detected with a detecting instrument (not illustrated) for each rotational angle (θ) of the sample, while rotating the disc-like sample 20 within an XY plane, thereby obtaining a θ-2θ X-ray diffraction chart.

Figure 3:
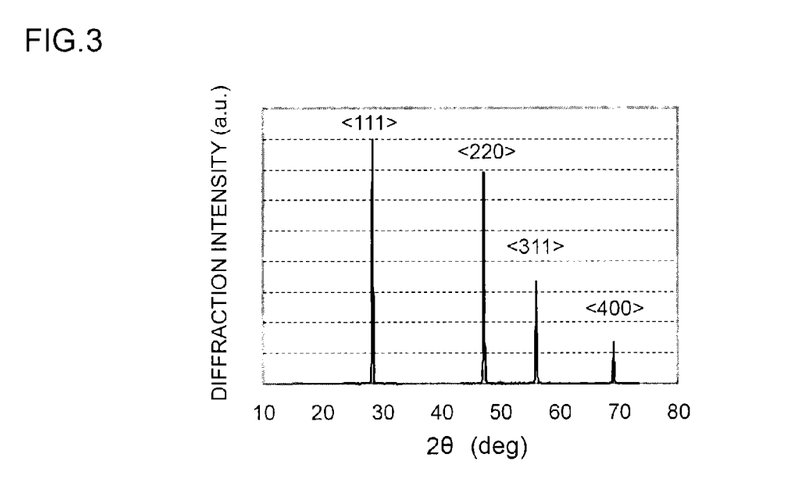
FIG. 3 is one example of a θ-2θ X-ray diffraction chart.

FIG. 3 is an example of the θ-2θ X-ray diffraction chart obtained as described above, where images of intense Bragg reflection from Miller index faces <111>, <220>, <311> and <400> appear as peaks in positions where 2θ=28.40°, 47.24°, 55.98° and 68.98°, respectively.

Figure 4:
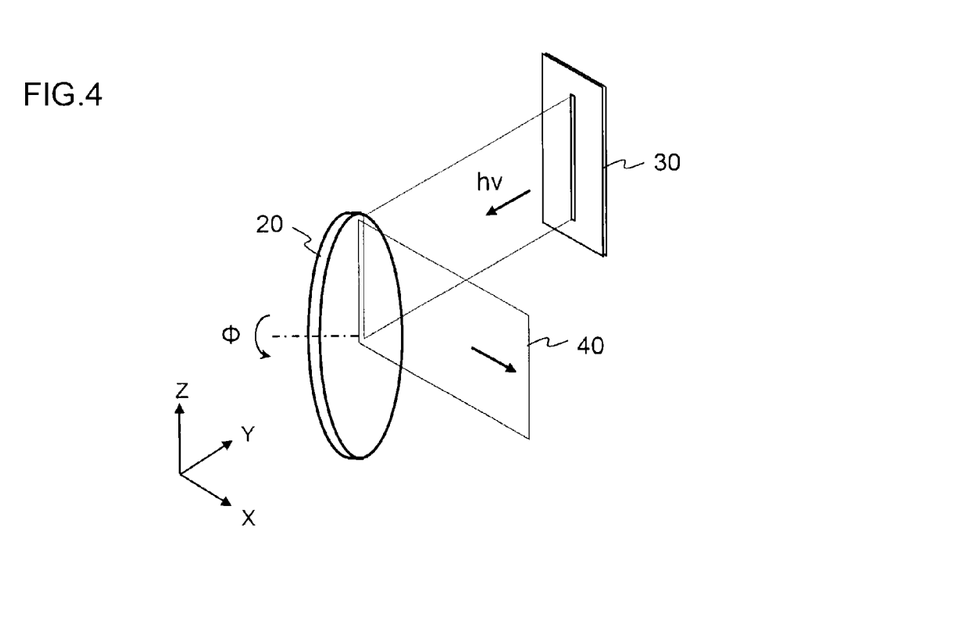
FIG. 4 is a drawing used to describe an outline of a measurement system used when a profile of X-ray diffraction from a plate-like sample is determined by a φ-scan method.

FIG. 4 is a drawing used to describe an outline of a measurement system used when a profile of X-ray diffraction from the disc-like sample 20 is determined by a so-called φ-scan method. For example, the abovementioned rotational angle θ of the disc-like sample 20 is set as an angle at which Bragg reflection from the Miller index face <111> is detected. Under this condition, X-rays are radiated to a thin, rectangular region defined by a slit in a region ranging from the center to a peripheral end of the disc-like sample 20, and the disc-like sample 20 is rotated within a YZ plane (φ=0° to) 360° with the center of the disc-like sample 20 as the center of rotation, so that this X-ray-radiated region scans over the entire surface of the disc-like sample 20.

Figure 5:
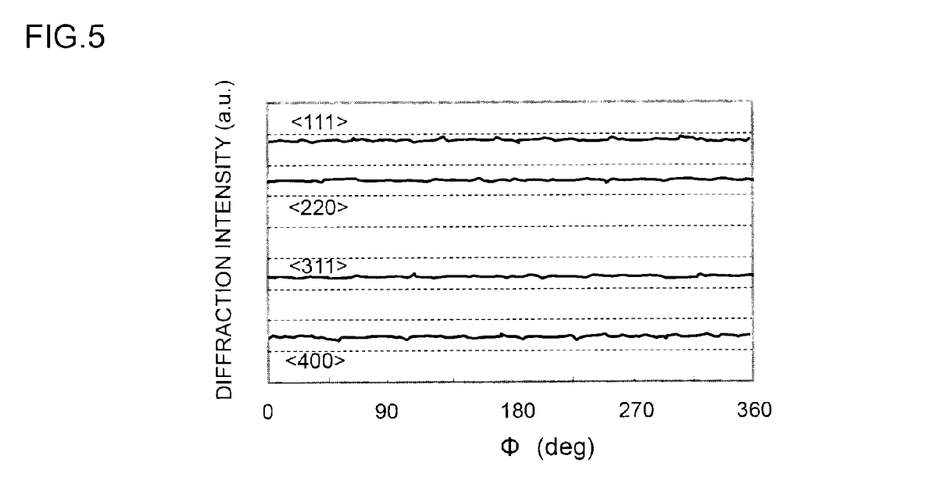
FIG. 5 is one example of a chart obtained by performing the φ-scan measurement illustrated in FIG. 4 with respect to Miller index faces <111>, <220>, <311> and <400>.

FIG. 5 is one example of a chart obtained by performing the above-described φ-scan measurement with respect to the Miller index faces <111>, <220>, <311> and <400>. In this example, Bragg reflection intensity is substantially constant no matter which of the abovementioned Miller index faces attention is focused on, and therefore, does not depend on the rotational angle φ. The chart is thus the same as that of the powder sample. That is, this disc-like sample 20 can be determined as being low in the degree of crystalline orientation (high in random orientation).

Figure 6:
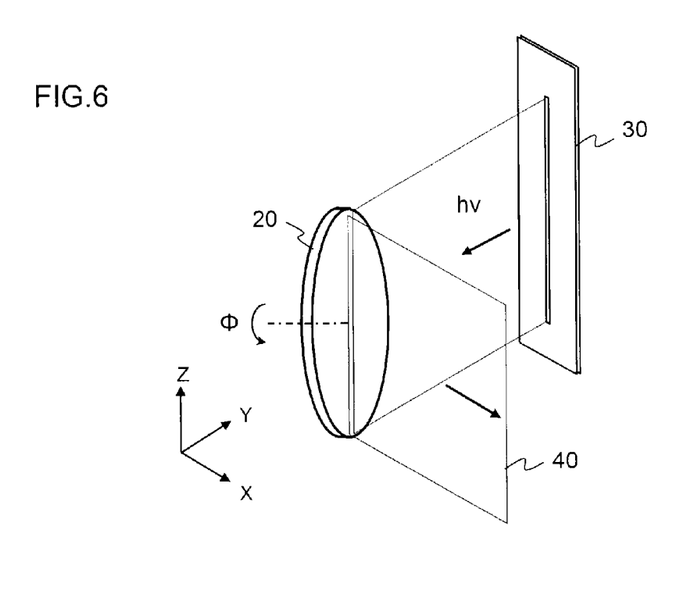
FIG. 6 is a drawing used to describe an outline of another measurement system used when a profile of X-ray diffraction from a plate-like sample is determined by a φ-scan method.

FIG. 6 is a drawing used to describe an outline of another measurement system used when a profile of X-ray diffraction from the disc-like sample 20 is determined by a φ-scan method. In the example illustrated in this figure, X-rays are radiated to a thin, rectangular region defined by a slit in a region of the disc-like sample 20 extending across two peripheral ends, and the disc-like sample 20 is rotated within a YZ plane (φ=0° to 360°) with the center of the disc-like sample 20 as the center of rotation, so that this X-ray-radiated region scans over the entire surface of the disc-like sample 20.

Figure 7:
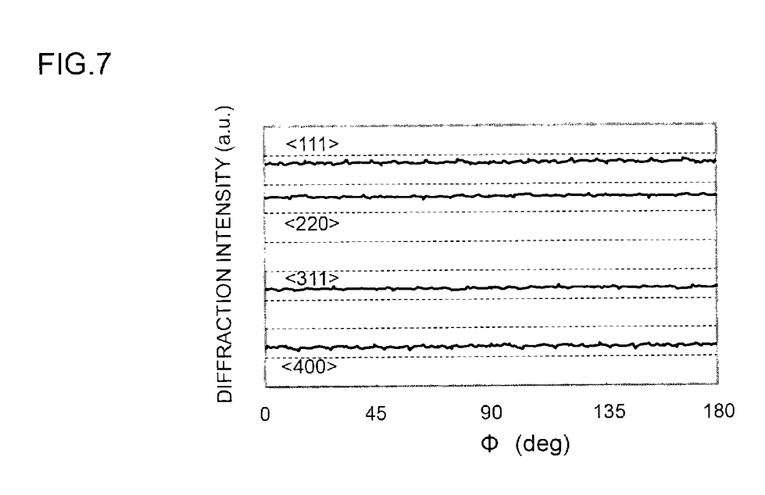
FIG. 7 is one example of a chart obtained by performing the φ-scan measurement illustrated in FIG. 6 with respect to Miller index faces <111>, <220>, <311> and <400>.

FIG. 7 is one example of a chart obtained by performing the above-described φ-scan measurement with respect to the Miller index faces <111>, <220>, <311> and <400>, where substantially the same φ-scan chart as the chart illustrated in FIG. 5 is obtained.

Figure 8:
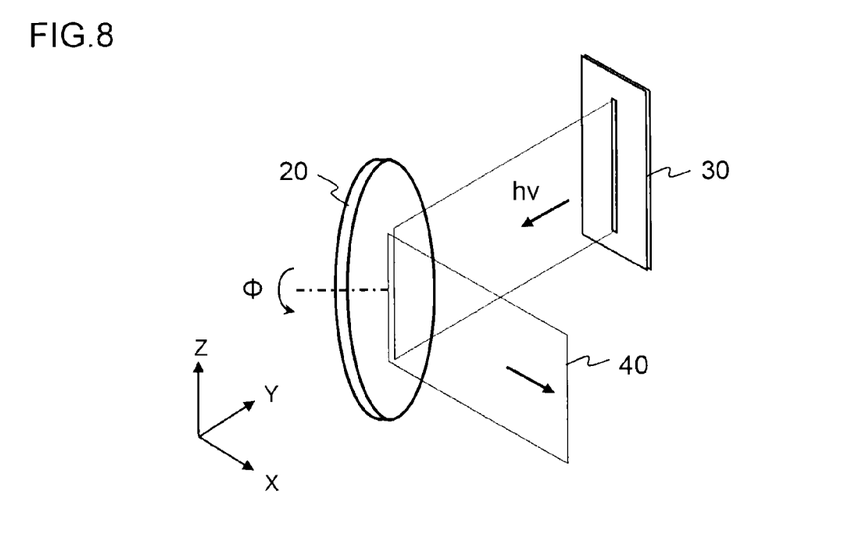
FIG. 8 is a drawing used to describe an outline of yet another measurement system used when a profile of X-ray diffraction from a plate-like sample is determined by a φ-scan method.

FIG. 8 is a drawing used to describe an outline of yet another measurement system used when a profile of X-ray diffraction from the disc-like sample 20 is determined by a φ-scan method. In the example illustrated in this figure, X-rays are radiated only to an inner circumferential region rather than the entire principal surface of the disc-like sample 20, and the disc-like sample 20 is rotated within a YZ plane (φ=0° to 360°) with the center of the disc-like sample 20 as the center of rotation, so that this X-ray-radiated region scans over the entire surface of the disc-like sample 20.

By performing such processing as determining the difference between a φ-scan chart available from such an X-ray-radiated region and the abovementioned φ-scan chart available from the principal surface of the disc-like sample 20 as a whole, it is possible to obtain an in-plane crystalline orientation distribution of the disc-like sample 20.

Whereas an in-plane crystalline orientation distribution is not considered to arise for disc-like samples 20 taken in such modes as illustrated in FIGS. 1A and 1B, it is needless to say that the evaluation of crystalline orientation according to the present invention is significant not only as a method for selecting a polycrystalline silicon rod grown by a Siemens method or the like, but also as a method for evaluating the degree of crystalline orientation of polycrystalline silicon by an X-ray diffraction method. Accordingly, by, for example, determining an in-plane crystalline orientation distribution with respect to a disc-like sample cut out parallel to the radial direction of a polycrystalline silicon rod grown by means of deposition based on a chemical vapor deposition method, it is possible to know the presence/absence of crystalline orientation within the polycrystalline silicon rod, a change in crystalline orientation with an increase in the diameter of the polycrystalline silicon rod, or the like. Consequently, it is possible to select polycrystalline silicon suitable as a raw material for the manufacture of monocrystalline silicon rod.

Specifically, in the above-described method for selecting a polycrystalline silicon rod, the Miller index face <hkl> is <111>. The method evaluates the diffraction intensity value of the baseline of the chart obtained by performing the above-described φ-scan for each of the two or more plate-like samples. If a value given by dividing the maximum value of the plurality of baseline diffraction intensity values by the minimum value thereof is 1.5 or smaller, the method selects the polycrystalline silicon rod as a raw material for the manufacture of monocrystalline silicon.

Alternatively, the Miller index face <hkl> may be <220>. The method may evaluate the diffraction intensity value of the baseline of the chart obtained by performing the above-described φ-scan for each of the two or more plate-like samples. If a value given by dividing the maximum value of the plurality of baseline diffraction intensity values by the minimum value thereof is 1.9 or smaller, the method may select the polycrystalline silicon rod as a raw material for the manufacture of monocrystalline silicon.

Yet alternatively, the method may perform the φ-scan with respect to both the Miller index faces <111> and <220> for each of the two or more plate-like samples, and evaluate a value (division value: $I^{<111>}/I^{<220>}$) given by dividing the diffraction intensity value ($I^{<111>}$) of the baseline of a chart obtained with respect to the Miller index face <111> by the diffraction intensity value ($I^{<220>}$) of the baseline of a chart obtained with respect to the Miller index face <220> to select the polycrystalline silicon rod as a raw material for the manufacture of monocrystalline silicon if the maximum value of a plurality of the division values determined from the two or more plate-like samples is smaller than 2.5.

Figure 9A:
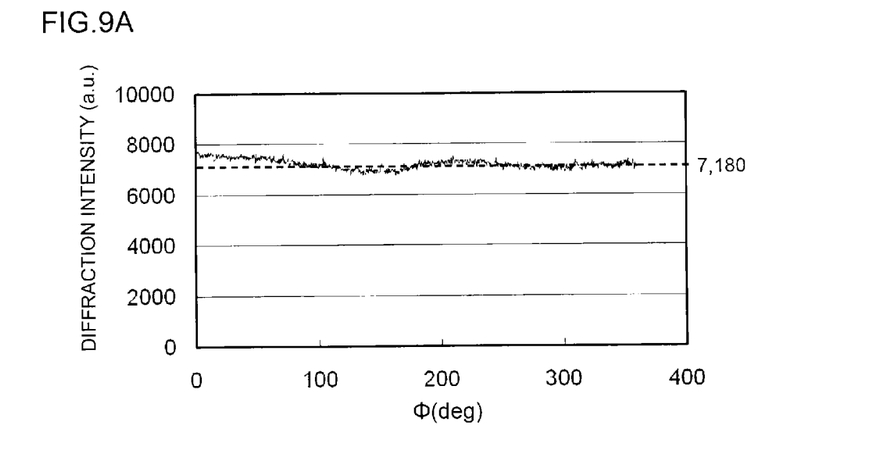
FIG. 9A is an example of a φ-scan chart with respect to the Miller index face <111> of a plate-like sample taken from the central part of a polycrystalline silicon rod.
Figure 9B:
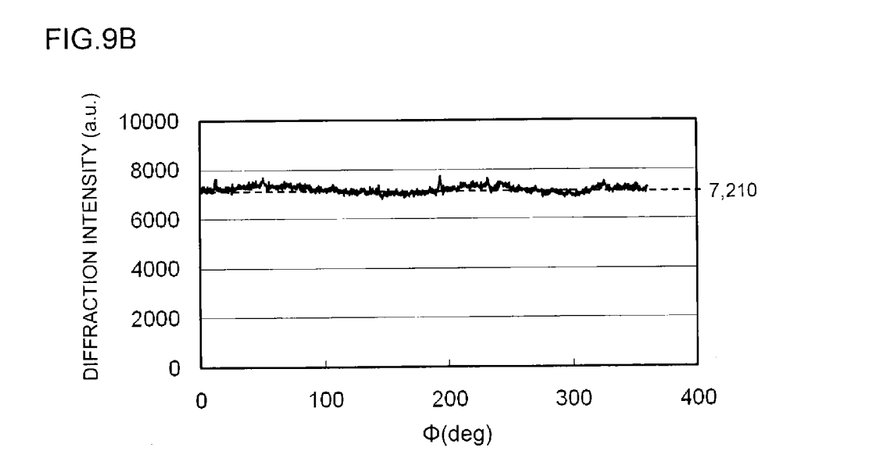
FIG. 9B is an example of a φ-scan chart with respect to the Miller index face <111> of a plate-like sample taken from the outer-peripheral part of a polycrystalline silicon rod.

Both FIGS. 9A and 9B are examples of φ-scan charts with respect to the Miller index face <111>, where FIG. 9A is a φ-scan chart of a plate-like sample taken from the central part of a polycrystalline silicon rod, whereas FIG. 9B is a φ-scan chart of a plate-like sample taken from a peripheral part of the same polycrystalline silicon rod. Note that these charts are obtained by the mode of measurement illustrated in FIG. 6 and show chart portions where many peaks do not appear for ease in understanding the meaning of the baseline.

Each line shown by a dotted line in these charts is the baseline. The crystalline orientation of polycrystalline silicon is evaluated on the basis of the diffraction intensity value (average) of this baseline. Note that the baseline of a chart portion where a peak is present is specified by first determining a peak having an S/N ratio of 3 or higher to be the peak, and then following a method used to determine a baseline when integrating peak intensity for peak portions.

EXAMPLES

Six polycrystalline silicon rods grown under different deposition conditions were prepared. Approximately 2 mm-thick disc-like samples ($20_{CTR}$, $20_{EDG}$ and $20_{R/2}$) were taken from the three locations illustrated in FIGS. 1A and 1B for each of these polycrystalline silicon rods (silicon rods A to F). Using the measurement system illustrated in FIG. 6, φ-scan charts of Miller index faces <111> and <220> were obtained. Note that the diameter of the disc-like samples 20 is approximately 20 mm.

Table 1 summarizes the diffraction intensity of a baseline (BL) for each of the disc-like samples obtained from these polycrystalline silicon rods and the presence/absence of the loss of crystal lines when monocrystalline silicon rods were grown by an FZ method using the polycrystalline silicon rods.

TABLE 1

| Silicon Rod | Plate-like Sample | BL Intensity (kcps) | | Max/Min | | Division Value | Loss of Crystal Lines |
|---|---|---|---|---|---|---|---|
| | | $I^{<111>}$ | $I^{<220>}$ | <111> | <220> | $I^{<111>}/I^{<220>}$ | |
| A | $20_{CTR}$ | 6.8 | 4.0 | 1.46 | 1.43 | 1.70 | No |
| | $20_{R/2}$ | 8.0 | 4.8 | | | 1.67 | |
| | $20_{EDG}$ | 9.9 | 5.7 | | | 1.74 | |
| B | $20_{CTR}$ | 7.5 | 3.1 | 1.47 | 1.84 | 2.42 | No |
| | $20_{R/2}$ | 9.5 | 4.7 | | | 2.02 | |
| | $20_{EDG}$ | 11.0 | 5.7 | | | 1.93 | |
| C | $20_{CTR}$ | 7.0 | 4.5 | 1.64 | 1.20 | 1.56 | Yes |
| | $20_{R/2}$ | 9.5 | 5.5 | | | 1.73 | |
| | $20_{EDG}$ | 11.5 | 4.6 | | | 2.50 | |
| D | $20_{CTR}$ | 6.0 | 2.8 | 2.33 | 1.89 | 2.14 | Yes |
| | $20_{R/2}$ | 10.0 | 4.5 | | | 2.22 | |
| | $20_{EDG}$ | 14.0 | 5.3 | | | 2.64 | |
| E | $20_{CTR}$ | 4.0 | 1.0 | 3.30 | 6.00 | 4.00 | Yes |
| | $20_{R/2}$ | 8.5 | 4.8 | | | 1.77 | |
| | $20_{EDG}$ | 13.2 | 6.0 | | | 2.20 | |
| F | $20_{CTR}$ | 7.8 | 2.5 | 1.92 | 2.00 | 3.12 | Yes |
| | $20_{R/2}$ | 11.0 | 4.0 | | | 2.75 | |
| | $20_{EDG}$ | 15.0 | 5.0 | | | 3.00 | |

For the silicon rod A, a value given by dividing the maximum value of a plurality of baseline diffraction intensity values by the minimum value thereof with respect to the Miller index face <111> is 1.5 or lower (1.46), and a value given by dividing the maximum value of a plurality of baseline diffraction intensity values by the minimum value thereof with respect to the Miller index face <220> is likewise 1.9 or lower (1.43). In addition, the division value ($I^{<111>}/I^{<220>}$) is smaller than 2.5 (1.74 maximum) for all of the plate-like samples.

For the silicon rod B, a value given by dividing the maximum value of a plurality of baseline diffraction intensity values by the minimum value thereof with respect to the Miller index face <111> is 1.5 or lower (1.47), and a value given by dividing the maximum value of a plurality of baseline diffraction intensity values by the minimum value thereof with respect to the Miller index face <220> is likewise 1.9 or lower (1.8). In addition, the division value ($I^{<111>}/I^{<220>}$) is smaller than 2.5 (2.42 maximum) for all of the plate-like samples.

For the silicon rod C, a value (1.64) given by dividing the maximum value of a plurality of baseline diffraction intensity values by the minimum value thereof with respect to the Miller index face <111> is larger than 1.5, whereas a value given by dividing the maximum value of a plurality of baseline diffraction intensity values by the minimum value thereof with respect to the Miller index face <220> is 1.9 or lower (1.20). In addition, the division value ($I^{<111>}/I^{<220>}$) is 2.5 or larger (2.50) in one of the three plate-like samples.

For the silicon rod D, a value (2.33) given by dividing the maximum value of a plurality of baseline diffraction intensity values by the minimum value thereof with respect to the Miller index face <111> is larger than 1.5, whereas a value given by dividing the maximum value of a plurality of baseline diffraction intensity values by the minimum value thereof with respect to the Miller index face <220> is 1.9 or lower (1.89). In addition, the division value ($I^{<111>}/I^{<220>}$) is 2.5 or larger (2.64) in one of the three plate-like samples.

For the silicon rod E, a value (3.30) given by dividing the maximum value of a plurality of baseline diffraction intensity values by the minimum value thereof with respect to the Miller index face <111> is larger than 1.5, and a value (6.00) given by dividing the maximum value of a plurality of baseline diffraction intensity values by the minimum value thereof with respect to the Miller index face <220> is likewise larger than 1.9. In addition, the division value ($I^{<111>}/I^{<220>}$) is larger than 2.5 (4.00) in one of the three plate-like samples.

For the silicon rod F, a value (1.92) given by dividing the maximum value of a plurality of baseline diffraction intensity values by the minimum value thereof with respect to the Miller index face <111> is larger than 1.5, and a value (2.00) given by dividing the maximum value of a plurality of baseline diffraction intensity values by the minimum value thereof with respect to the Miller index face <220> is likewise larger than 1.9. In addition, the division value ($I^{<111>}/I^{<220>}$) is larger than 2.5 for all of the three plate-like samples.

Whereas any loss of crystal lines was not observed in the silicon rods A and B when monocrystalline silicon rods were grown by an FZ method, loss of crystal lines occurred in the silicon rods C, D, E and F.

A study made by the present inventors has confirmed that even if polycrystalline silicon the crystal grains of which are not observed by such a visual observation as disclosed in Patent Literature 2 is used as a raw material to manufacture monocrystalline silicon, loss of crystal lines due to the induction of dislocation generation occurs in some cases. On the other hand, the study has confirmed that according to the above-described method of the present invention, it is possible to prevent loss of crystal lines with high certainty, if monocrystalline silicon is produced using a polycrystalline silicon rod or a polycrystalline silicon ingot selected with the above-described criteria.

In particular, a polycrystalline silicon rod, such as the abovementioned silicon rod A or B, in which a value given by dividing the maximum value of a plurality of baseline diffraction intensity values by the minimum value thereof with respect to the Miller index face <111> is 1.5 or lower (1.46), a value given by dividing the maximum value of a plurality of baseline diffraction intensity values by the minimum value thereof with respect to the Miller index face <220> is likewise 1.9 or lower, and the division value ($I^{<111>}/I^{<220>}$) smaller than 2.5 for all of plate-like samples, is suitable as a raw material for producing monocrystalline silicon.

INDUSTRIAL APPLICABILITY

The present invention provides a technique of selecting polycrystalline silicon suitable as a raw material for the manufacture of monocrystalline silicon with high degrees of quantitativeness and repeatability and contributing to the stable manufacture of monocrystalline silicon.

REFERENCE SIGNS LIST

1: Silicon core wire
10: Polycrystalline silicon rod
11: Rod
20: Plate-like sample
30: Slit
40: X-ray beam

The invention claimed is:

1. A method for evaluating the degree of crystalline orientation of polycrystalline silicon by an X-ray diffraction method, the evaluating method comprising:
   forming the polycrystalline silicon into a plate-like sample;
   disposing the plate-like sample in a position where Bragg reflection from a Miller index face <hkl> is detected;
   performing in-plane rotation of the plate-like sample at a rotational angle φ with the center of the plate-like sample as the center of rotation, so that an X-ray-radiated region defined by a slit φ-scans over the principal surface of the plate-like sample, to determine a chart representing the dependence of the intensity of Bragg reflection from the Miller index face <hkl> on the rotational angle (φ) of the plate-like sample;
   determining a baseline from the chart; and
   using the diffraction intensity value of the baseline as the estimative index of the degree of crystalline orientation.

2. The method for evaluating the degree of crystalline orientation of polycrystalline silicon according to claim 1, wherein the Miller index face <hkl> is at least one of <111> and <220>.

3. A method for selecting a polycrystalline silicon rod to be used as a raw material for the manufacture of monocrystalline silicon using an X-ray diffraction method, wherein the polycrystalline silicon rod is grown by means of deposition based on a chemical vapor deposition method, the selecting method comprising:
   obtaining two or more plate-like samples having a cross-section perpendicular to the radial direction of the polycrystalline silicon rod as a principal surface;
   disposing the plate-like samples in a position where Bragg reflection from a Miller index face <hkl> is detected;
   performing in-plane rotation of the plate-like samples at a rotational angle φ with the center of the plate-like sample as the center of rotation, so that an X-ray-radiated region defined by a slit φ-scans over the principal surface of the plate-like sample, to determine a chart representing the dependence of the intensity of Bragg reflection from the Miller index face <hkl> on the rotational angle φ of the plate-like sample;
   determining baselines from the chart; and determining suitability/unsuitability as a raw material for the manufacture of monocrystalline silicon using the results of comparison between or among diffraction intensity values of the baselines obtained from the respective two or more plate-like samples as criteria, wherein the Miller index face <hkl> is <111>, and the method further comprises determining the diffraction intensity value of the baseline of the chart obtained by performing the φ-scan for each of the two or more plate-like samples and selecting the polycrystalline silicon rod as a raw material for the manufacture of monocrystalline silicon if a value given by dividing the maximum value of baseline diffraction intensity values by the minimum value thereof is 1.5 or smaller.

4. A method for selecting a polycrystalline silicon rod to be used as a raw material for the manufacture of monocrystalline silicon using an X-ray diffraction method, wherein the polycrystalline silicon rod is grown by means of deposition based on a chemical vapor deposition method, the selecting method comprising:
   obtaining two or more plate-like samples having a cross-section perpendicular to the radial direction of the polycrystalline silicon rod as a principal surface;
   disposing the plate-like samples in a position where Bragg reflection from a Miller index face <hkl> is detected;
   performing in-plane rotation of the plate-like samples at a rotational angle $\phi$ with the center of the plate-like sample as the center of rotation, so that an X-ray-radiated region defined by a slit $\phi$-scans over the principal surface of the plate-like sample, to determine a chart representing the dependence of the intensity of Bragg reflection from the Miller index face <hkl> on the rotational angle ($\phi$) of the plate-like sample;
   determining baselines from the chart; and determining suitability/unsuitability as a raw material for the manufacture of monocrystalline silicon using the results of comparison between or among diffraction intensity values of the baselines obtained from the respective two or more plate-like samples as criteria, wherein the Miller index face <hkl> is <220>, and the method further comprises determining the diffraction intensity value of the baseline of the chart obtained by performing the $\phi$-scan for each of the two or more plate-like samples and selecting the polycrystalline silicon rod as a raw material for the manufacture of monocrystalline silicon if a value given by dividing the maximum value of the plurality of baseline diffraction intensity values by the minimum value thereof is 1.9 or smaller.

5. A method for selecting a polycrystalline silicon rod to be used as a raw material for the manufacture of monocrystalline silicon using an X-ray diffraction method, wherein the polycrystalline silicon rod is grown by means of deposition based on a chemical vapor deposition method, the selecting method comprising:
   obtaining two or more plate-like samples having a cross-section perpendicular to the radial direction of the polycrystalline silicon rod as a principal surface;
   disposing the plate-like samples in a position where Bragg reflection from a Miller index face <hkl> is detected;
   performing in-plane rotation of the plate-like samples at a rotational angle $\phi$ with the center of the plate-like sample as the center of rotation, so that an X-ray-radiated region defined by a slit $\phi$-scans over the principal surface of the plate-like sample, to determine a chart representing the dependence of the intensity of Bragg reflection from the Miller index face <hkl> on the rotational angle ($\phi$) of the plate-like sample;
   determining baselines from the chart; and determining suitability/unsuitability as a raw material for the manufacture of monocrystalline silicon using the results of comparison between or among diffraction intensity values of the baselines obtained from the respective two or more plate-like samples as criteria, wherein the Miller index faces <hkl> are <111> and <220>, further comprising: performing the $\phi$-scan on both the Miller index faces <111> and <220> for each of the two or more plate-like samples; dividing the diffraction intensity value ($I^{<111>}$) of the baseline of a chart obtained with respect to the Miller index face <111> by the diffraction intensity value ($I^{<220>}$) of the baseline of a chart obtained with respect to the Miller index face <220> to determine a value (division value: $I^{<111>}/I^{<220>}$) and selecting the polycrystalline silicon rod as a raw material for the manufacture of monocrystalline silicon if the maximum value of a plurality of the division values determined from the two or more plate-like samples is smaller than 2.5.

6. The method for selecting a polycrystalline silicon rod according to claim 3, wherein the polycrystalline silicon rod is grown by a Siemens method.

7. A polycrystalline silicon rod selected by the method according to claim 3.

8. A polycrystalline silicon ingot obtained by crushing the polycrystalline silicon rod according to claim 7.

9. A method for manufacturing monocrystalline silicon using the polycrystalline silicon rod according to claim 7 as a silicon feedstock.

10. A method for manufacturing monocrystalline silicon using the polycrystalline silicon ingot according to claim 8 as a feedstock.

11. The method for selecting a polycrystalline silicon rod according to claim 4, wherein the polycrystalline silicon rod is grown by a Siemens method.

12. A polycrystalline silicon rod selected by the method according to claim 4.

13. A polycrystalline silicon ingot obtained by crushing the polycrystalline silicon rod according to claim 12.

14. A method for manufacturing monocrystalline silicon using the polycrystalline silicon rod according to claim 12 as a silicon feedstock.

15. A method for manufacturing monocrystalline silicon using the polycrystalline silicon ingot according to claim 13 as a feedstock.

16. The method for selecting a polycrystalline silicon rod according to claim 5, wherein the polycrystalline silicon rod is grown by a Siemens method.

17. A polycrystalline silicon rod selected by the method according to claim 5.

18. A polycrystalline silicon ingot obtained by crushing the polycrystalline silicon rod according to claim 17.

19. A method for manufacturing monocrystalline silicon using the polycrystalline silicon rod according to claim 17 as a silicon feedstock.

20. A method for manufacturing monocrystalline silicon using the polycrystalline silicon ingot according to claim 18 as a feedstock.

* * * * *